United States Patent [19]

Cerny

[11] Patent Number: 4,560,519

[45] Date of Patent: Dec. 24, 1985

[54] SELF-CONTAINED NEBULIZER AND SYSTEM

[75] Inventor: David E. Cerny, Hoffman Estates, Ill.

[73] Assignee: Respiratory Care, Inc., Arlington Heights, Ill.

[21] Appl. No.: 500,812

[22] Filed: Jun. 3, 1983

[51] Int. Cl.$^4$ .................. B01F 3/04; A61M 11/02
[52] U.S. Cl. .................. 261/78 A; 128/200.18; 128/200.21; 239/338; 261/65; 261/116
[58] Field of Search .................. 261/78 A, 116, 142, 261/65, DIG. 65; 239/338, 366; 128/200.18, 200.21

[56] References Cited

U.S. PATENT DOCUMENTS

| | | | |
|---|---|---|---|
| 3,097,645 | 7/1963 | Lester | 261/116 X |
| 3,584,621 | 6/1971 | Bird et al. | 128/200.18 |
| 3,762,409 | 10/1973 | Lester | 261/78 A X |
| 3,826,255 | 7/1974 | Havstad et al. | 261/DIG. 65 |
| 3,874,379 | 4/1975 | Enfield et al. | 261/DIG. 65 |
| 4,116,387 | 9/1978 | Kremer, Jr. et al. | 239/366 X |
| 4,150,071 | 4/1979 | Pecina | 261/DIG. 65 |
| 4,198,969 | 4/1980 | Virag | 261/DIG. 65 |
| 4,231,973 | 11/1980 | Young et al. | 261/DIG. 65 |
| 4,259,951 | 4/1981 | Chernack et al. | 128/200.18 X |
| 4,333,450 | 6/1982 | Lester | 128/200.18 X |

Primary Examiner—Richard L. Chiesa
Attorney, Agent, or Firm—Eric P. Schellin

[57] ABSTRACT

A nebulizer system including a self-contained system including a nebulizer. The nebulizer includes a cylindrical housing having a bottom which has axially and centrally located gas conduit extending therefrom and terminating in a nozzle internally of said housing. The housing has mounted therein a funnel shaped wall the apex of which has a conduit of a wider dimension to encompass said nozzle in axial and spaced alignment therewith. The conduit terminates in a spray opening whereby liquid in a reservoir defined by the housing bottom and funnel shaped wall is picked up by the gas emanating from the nozzle. The liquid-gas mixture is discharged above the funnel wall against a protrusion and is distributed therefrom against an annular baffle depending from the top of the housing. The aerosol thereby produced is discharged through an opening into a conduit system for delivery to a patient directly or as a part of a ventilator or intermittent positive breathing apparatus of known types.

13 Claims, 19 Drawing Figures

SELF-CONTAINED NEBULIZER AND SYSTEM

BACKGROUND OF THE INVENTION

The invention relates to a new and improved liquid nebulizing device and more particularly relates to a disposable, preferably constructed of a transparent plastic, nebulizer having improved aerosol production and a system therefor.

It is well known that nebulizers are pneumatic devices for breaking up a liquid medicament into small particles and to entrain such small liquid particles in the stream of air or oxygen gas thereby providing an aerosol for inhalation therapy in the treatment of respiratory system disorders or to avoid such disorders. It is important during such therapy that there be a sufficient quantity and proper formation of aerosol provided by the nebulizer. If the particles or droplets of the medicament are too fine, they are not likely to be retained in the respiratory tract, but will, to a great extent, be exhaled. If the particles are too large, they will-likely be deposited on the upper reaches of the respiratory system, such as the trachea and the upper tracheal-bronchial trees, thereby leaving the rest of the system untreated. It is also important that the aerosol be delivered to the patient in a smooth, uniform manner.

Production of a proper aerosol is substantially dependent on the design of the nebulizer. Prior to such patents as U.S. Pat. Nos. 3,097,645 and 3,762,409, it was conventional to employ the fly-spray principle of aerosol in the design of nebulizers. This principle involved directing a stream of gas from a nozzle at right angles across the open end of a tube extending to the reservoir containing liquid medicament. Proper positioning and sizing of the tube and nozzle are extremely critical and the design of a nebulizer employing the principle is such that it is difficult and expensive to manufacture, particularly if the nebulizer is to be made of plastic.

Nebulizers of the type as shown in Lester's patents mentioned in the above and of the present nebulizer is that these types of nebulizers are simple and inexpensive to manufacture. Also, the design of these nebulizers are such that the device can be easily formed of plastic and the device is relatively unbreakable. Moreover, because these types of nebulizers can be produced at a marked reduction in cost, the entire nebulizer can be disposed of after use thereby avoiding the costs of cleaning.

The present invention represents an improved form of this particular type of nebulizer and employs certain elements of these nebulizers. However, the present invention also includes numerous details of construction not shown in any previous nebulizer devices which produce new and improved results.

SUMMARY OF THE INVENTION

The nebulizer of the present invention provides improved aerosol production and possesses improved operating characteristics. The nebulizer includes an enclosed container having an aerosol outlet in its cover, a nozzle assembly extending into the container having a gas orifice and a spray orifice spaced from and coaxial with the gas orifice, and a diffuser baffle assembly positioned within the container in the spray path of the spray orifice. When gas is passed through the gas orifice, liquid is drawn from the container into the space between the orifices and then carried in the form of small particles through the spray orifice. A diffuser assembly is provided consisting of a centrally located nose portion terminating axially from said spray orifice in spaced relationship therewith. The nose portion is surrounded concentrically with an annular baffle terminating in a downwardly projecting edge portion which terminates in a plane below the spray orifice. The annular portion connecting the nose portion and the annular baffle is arcuate. The baffle prevents oversize liquid particles from passing out through the aerosol outlet.

Means is also provided for returning any accumulation of excess liquid to its reservoir through a suitably disposed partition. The said partition also is useful in insuring that liquid is not spilled into the aerosol outlet even if the nebulizer is on its side.

Additionally, the nebulizer has great efficacy in that it can be used in various systems requiring aerosol delivery. For instance, it can be used with regard to positive ventilators or with simple delivery systems.

DETAILED DESCRIPTION OF THE INVENTION

Figure 3:
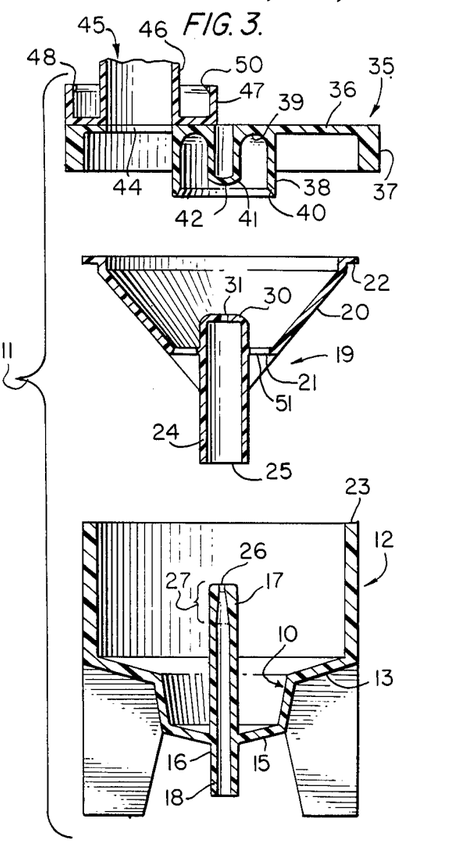
FIG. 3 is a cross-sectional view of a nebulizer wherein the parts are exploded.
Figure 4:
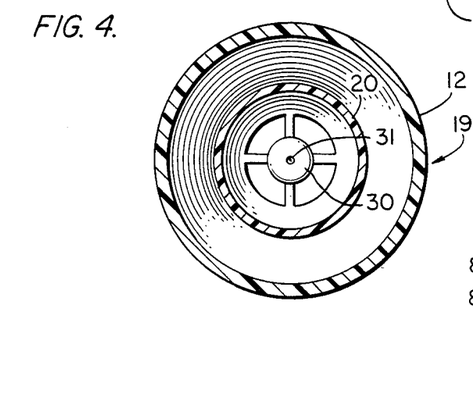
FIG. 4 is a cross-sectional view of the nebulizer taken along line 4—4 of FIG. 2.

Attention is directed to FIG. 3 and related figures for an understanding of one embodiment of the nebulizer 11 per se. It will be seen that the nebulizer of FIG. 3 is depicted in an exploded fashion. To the right side of FIG. 2 it is depicted in its assembled position. It is pointed out that vertical and horizontal designations hereinafter is to establish positions for elucidation and does not necessarily mean that the elements so designated must be positioned in a particular manner.

The nebulizer 11 consists of three basic parts that are designed to interfit. A main cylindrical body 12 has an inwardly downwardly sloping bottom 10 having a first annular sloping portion 13, inwardly concentric therewith a second more severely annular sloping wall 14 and finally yet another less severe annular sloping wall 15 positioned inwardly and concentric with the second sloping wall 14. The lower portion defines a space from 0 to 5 ml. while the lower portion and the wider upper portion together define a volume of 0 to 25 ml.

Centrally and axially disposed is a tubular conduit 16 having an upwardly extending nozzle 17 which extends for a distance into the cylindrical body 12. The tubular conduit 16 also has a tubular portion 18 extending downwardly out of the bottom 10. The tubular portion 18 is adapted and constructed to accept a usually flexible conduit (not shown) through which pressurized gas is transmitted which is to be entrained with moisture.

The second component 19 is adapted and constructed to be fitted into the body and has a funnel configuration with an inwardly downwardly annular sloping wall 20 with an inner concentric annular flat portion 21. The uppermost portion of the second component 19 has an annular flat radially extending flange 22, suitably dimensioned whereby when assembled into main cylindrical body 12 rests on its underside on the upwardly extending edge 23 of the main cylindrical body 12.

The second component 19 has a downwardly extending concentric central tubular conduit portion 24 terminating in a downwardly facing open end 25. The internal diameter is such that it fits over the upwardly extending nozzle 17 in spaced relationship thereto whereby an annular space is formed between said nozzle 17 and said tubular conduit portion 24.

The upwardly extending nozzle 17 terminates in an upwardly facing axially aligned orifice 26 which has a diameter less than most of the internal diameter of the conduit 16. As a matter of fact it has been found most efficacious to gradually progressively diminish the normal internal diameter of conduit 16 to the diameter of said upwardly facing opening 26 over a terminal portion 27 by providing an internal cone over said terminal portion wherein the apex angle is about 20°.

The upper portion of tubular conduit portion 24 terminates in an upper horizontal wall 30 having an axially centrally disposed orifice 31. The said wall 30 is vertically and axially displaced from the upwardly facing opening 26 whereby there is a continuum of spacing between conduit 24 and the upwardly extending nozzle 17 as further mentioned in the above.

The orifice 26 of conduit nozzle 17 is considerably smaller than the orifice 31 of conduit 24.

The conduit 24 is of a linear dimension whereby when the second component 19 is assembled with the cylindrical body 12, it terminates short of annular sloping wall 15. By this construction, liquid contained in the cylindrical body 12 may migrate upwardly between the aforementioned space defined by conduit nozzle 17 and conduit 24. In an alternate embodiment the conduit 24 may rest on the said sloping wall 15 and the lowermost end portion of conduit 24 is then supplied with openings for the passage of liquid into the afore-mentioned space.

The nebulizer 11 has a closure 35 having a roof 36 and downwardly depending therefrom a skirt 37. The internal diameter of the skirt 37 is slightly larger than the outer diameter of the cylindrical body 12 whereby the closure 35 closes the said cylindrical body. The radially extending flange 22 of the second component 19 which rests on the upwardly facing edge 23 is sandwiched between the said edge and an annular portion of the underside of the roof 36 of the closure 35. The various components are fixedly secured as by adhesives or may be screwed together when conventional screw threads are provided or screw lug means may be provided of a conventional nature.

The closure 35 is also supplied with a concentrically disposed skirt 38 which is also downwardly depending from the roof 36. The skirt 38 has an inwardly facing bevelled edge 40. The skirt 38 has an axial downward dimension whereby when said components are assembled it terminates slightly below the upward terminus of conduit 24. It is pointed out, however, that the higher the skirt 38, the larger will be the particles while on the other hand the lower the skirt, the smaller will be the particles.

Axially and centrally disposed from the said roof 36 is a cylindrical member 41 depending from the said roof. The cylindrical member 41 terminates in a rounded end 42 and short of the end wall 30 of conduit 24. The rounded end 42 acts as a nose baffle or protrusion upon which fluid is impinged when said nebulizer is in operation.

The underside of the roof 36 located between the skirt 38 and the cylindrical member 41 has an annular ring of an arcuate wall 39 to provide a smooth rounded transition from the cylindrical wall of member 41 and the internal wall of skirt 38.

Closure 35 is supplied off center, with an egress port 44 around which is secured a tubular seal member 45 which is suitably affixed to the top of roof 36 or may be integrally formed therewith. The tubular seal member has a first upstanding elongated cylindrical member 46 and outwardly thereof, and concentrically, a second upstanding elongated cylindrical member 47. The former has a larger axial dimension than the latter. The annular space 48 defined between said respective cylindrical members is designed to accept the end portion of a tubular conduit from a tubular fluid transmission means, more about which will be elucidated below. To facilitate in the retaining of such a fluid transmission means, the inwardly facing portion of skirt 47 is supplied with an inwardly facing annular bead 50 adapted and constructed to mate with a suitably disposed annular radially extending groove appropriately positioned on said tubular transmission means.

Of further interest is the fact that annular flat portion 21 of component 19 has a plurality of drain holes 51 whereby there is a communication between the upperside of component 19 and therebelow.

Prior to assembling, the nebulizer is charged with water. The water is contained in the cylindrical body 12. When fully charged the level therein should be below the flat portion 21 so that the water does not flow upwardly in a reverse fashion through the drain holes 51 even when the nebulizer is lying on its side.

In operation, air or oxygen is delivered under pressure through conduit 16 and through orifice 26 which acts as a venturi orifice to draw up water around the previously mentioned space and entrains the water as fine droplets or mist. The so entrained water and gas mixture emanates from orifice 31 and impinges on nose baffle 42. The rounded surface thereof deflects most of the stream outwardly radially against the inner wall of skirt 38 and beyond bevelled edge 40, thereby forcing the moving stream to make a 180° turn downwardly before being able to progress to the egress port 44.

The larger droplets of water not strongly entrained will drop out in view of the rather tortuous path described. These droplets will accumulate on the surface defined by the upper surface of the inwardly downwardly sloping wall 20 of the component 19 and on the underside of roof 36 of the closure 35. The droplets, when of sufficient quantity will accumulate and will drain through the drain holes 51, thereby permitting the return of excess water back into the cylindrical body 12.

The nebulizer of the present invention may be employed to feed a conduit transmission system to supply moisturized air or oxygen to a patient requiring treatment.

The nebulizer, as has been stated, is supplied with a tubular connecting means for suitable transmission as desired and required for various types of breathing inhalation systems having breathing enhancement means or not.

Figures 1, 2:
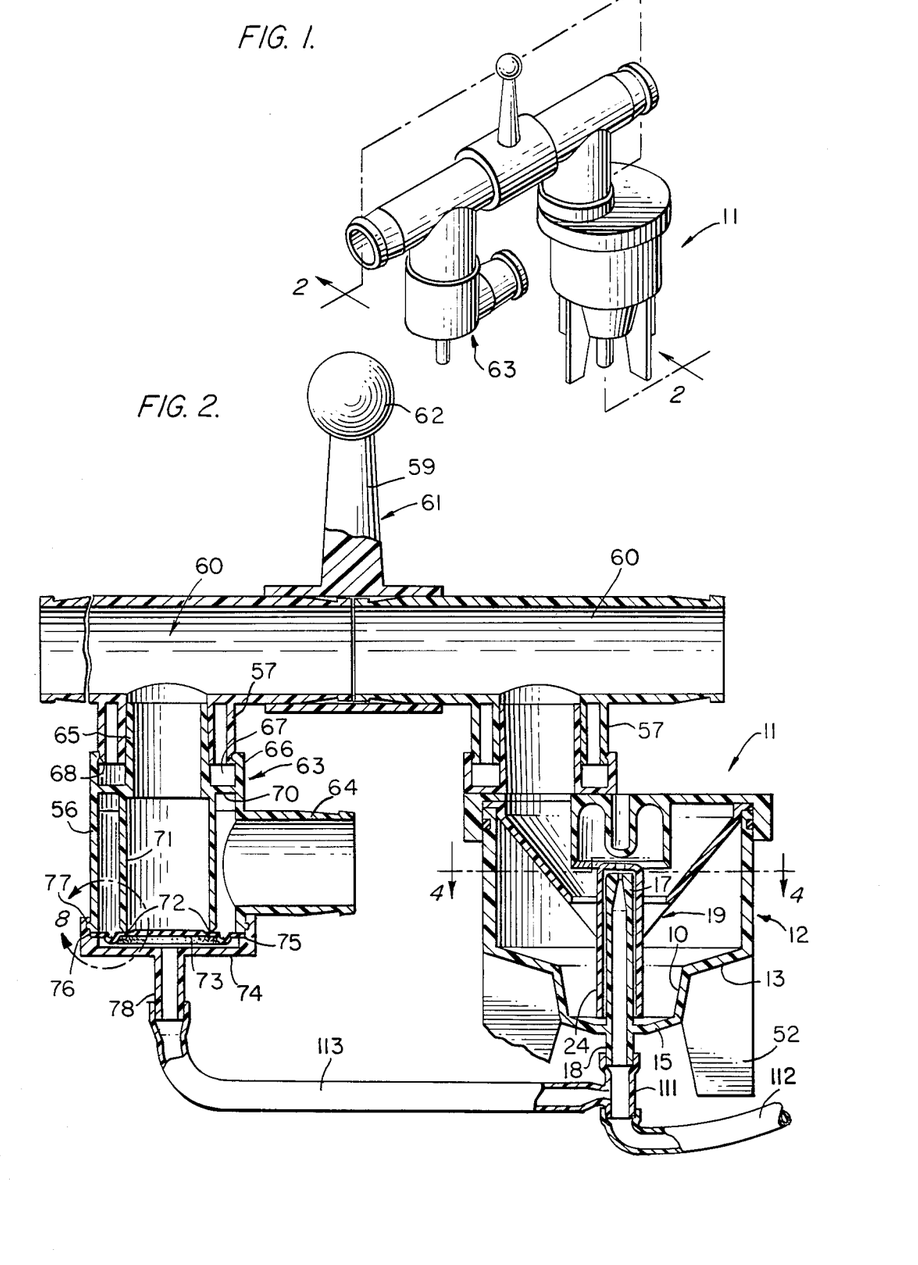
FIG. 1 is a perspective view of the present invention.
FIG. 2 is a cross-sectional view of the device of the present invention taken along line 2—2 of FIG. 1.

For instance, the system shown in FIGS. 1 and 2 pertain to a system having a particular transmission, but the nebulizer of the present invention is not limited to such use. On the contrary, the structure shown is for purposes of illustrating the physical components that may be employed to assemble a system as desired.

For instance, in regard to FIGS. 1 and 2, it will be noted that the system consists of five major components, two of which are duplicates of one another. First, is depicted the nebulizer 11 of the present invention. Next, is a first manifold tee piece 60 having its depending leg 57 in communication with the nebulizer 11. The first manifold tee piece 60 has one arm connected to an arm of amother similarly constructed second manifold tee piece 60. The two arms are held in cooperative engagement by a tubular connector hanger 61 having an outwardly radially extending arm 59 terminating in a knob 62 for connection to a hanger means (not shown). The hanger will be discussed with greater particularity in conjunction with FIGS. 16 and 17.

It will be noted that the downwardly depending leg 57 of the second manifold tee piece 60 is connected to an exhaust valve body 63 designed to dump the gases when there is an unwarranted back pressure.

Figures 8, 9, 10, 11:
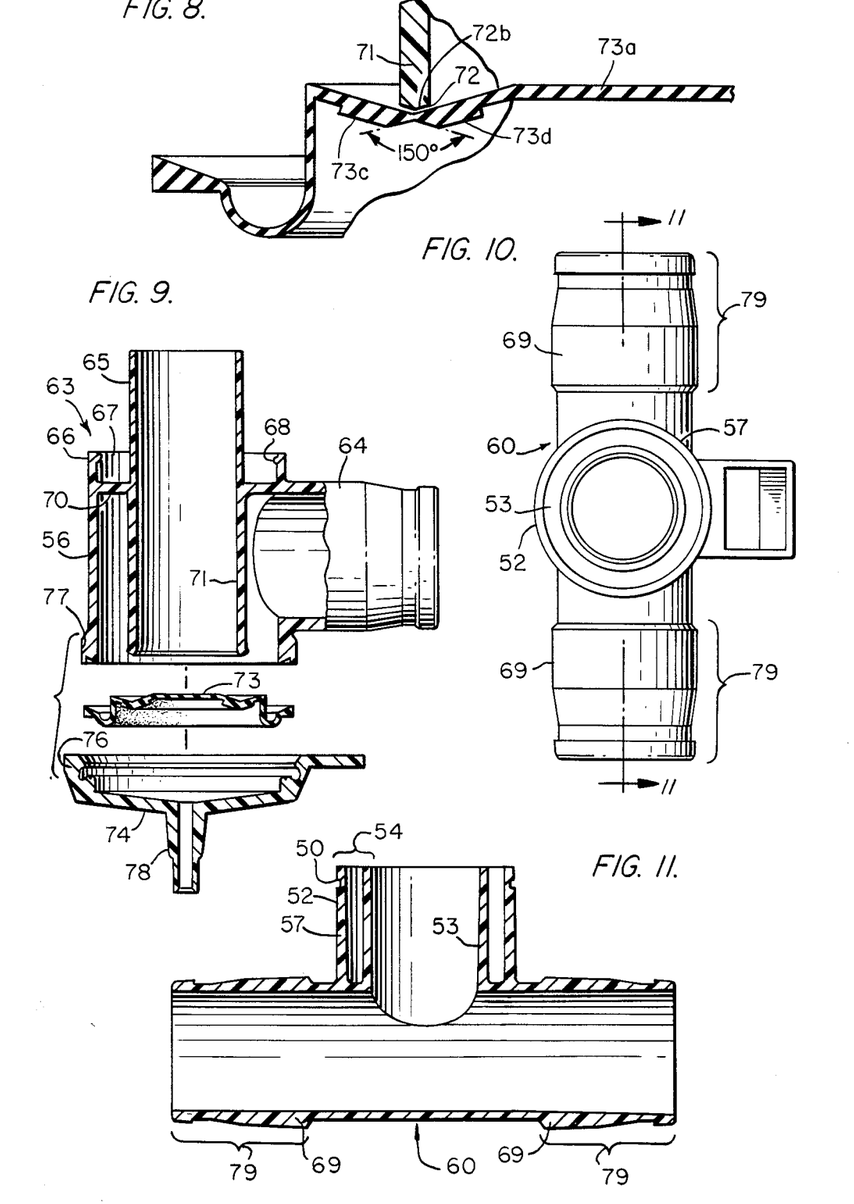
FIG. 8 is an enlarged fragmentary and sectional view of the diaphragm of the valve arrangement used in the exhaust valve body.
FIG. 9 is a side view partially in cross-section of the exhaust valve body with the diaphragm valve and cap exploded therefrom in cross-section.
FIG. 10 is a bottom view of the manifold tee piece.
FIG. 11 is a cross-sectional view of the manifold tee piece taken along line 11—11 of FIG. 10.

Attention is directed to FIGS. 10 and 11. The downwardly depending legs 57 of the manifold tee piece 60 comprise a concentric double wall portion of outer cylindrical tube 52 and inner cylindrical tube 53 open at 54 of the downwardly terminating portion. Both cylindrical tubes 52 and 53 of the open end portion 54 of the leg 57 is adapted and constructed to fit into the annular space defined by upstanding cylindrical members 46 and 47 and is fixedly secured thereinto. It will be seen that the axial length of cylindrical member 46 is useful in controlling the amount of spacing for the connection being made between the nebulizer and manifold tee piece 60.

The fitment of the leg end portion 54 is made quite secure even with only a snap fit as the outer cylindrical tube 52 and inner cylindrical tube 53 is under slight tension when pressed into the annular space 48.

The other legs 69 of the manifold tee piece 60 extend in opposite directions. Suitable annular detents 79 are provided to which a flexible conduit hose may be connected thereon or one or more of the said other legs 69 may be inserted into a connector hanger 61.

Figure 5:
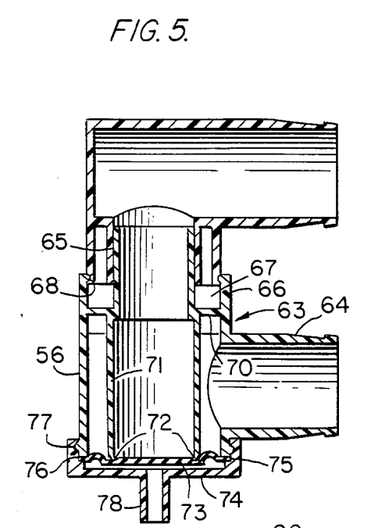
FIG. 5 is a cross-sectional view of an elbow conduit connection means and of the exhaust valve body.
Figure 6:
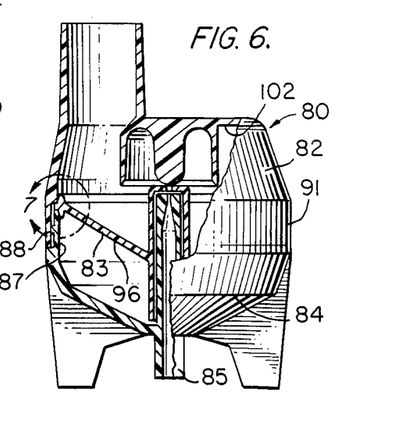
FIG. 6 is another embodiment of the nebulizer portion of the present invention partially in cross-sections.
Figure 7:
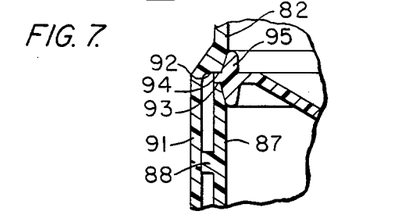
FIG. 7 is a view of a cross-sectional fragmentary portion of said other embodiment.
Figure 12:
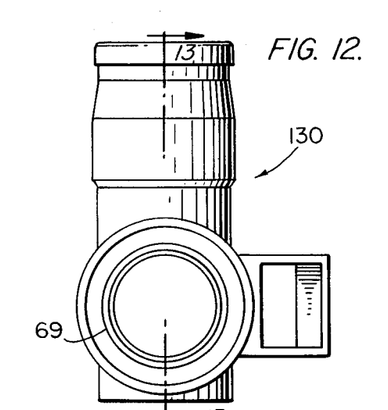
FIG. 12 is a bottom view of an elbow connector.
Figure 13:
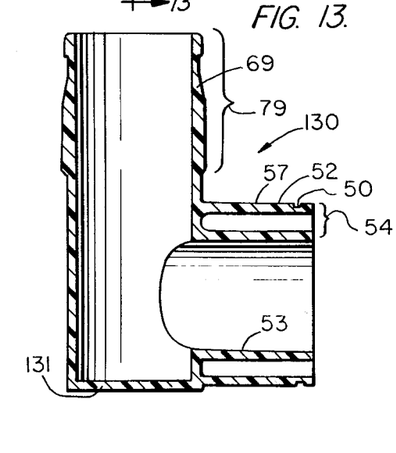
FIG. 13 is a cross-sectional view of the exhaust manifold taken along line 13—13 of FIG. 14.

Attention is now directed to FIGS. 12 and 13. These two figures depict an elbow conduit 130. The elbow conduit 130 is useful when the flow passage in one direction is to terminate in an exhaust valve body 63 only, as shown in FIG. 5, for instance. The elbow conduit 130 is essentially identical in structure as the manifold tee piece 60 except that instead of a complete pass through tubular conduit section it terminates on one side of leg 57 with a wall 131. the leg 57 has a U-shaped means 120 for connection to a hanger connector 61.

Figure 14:
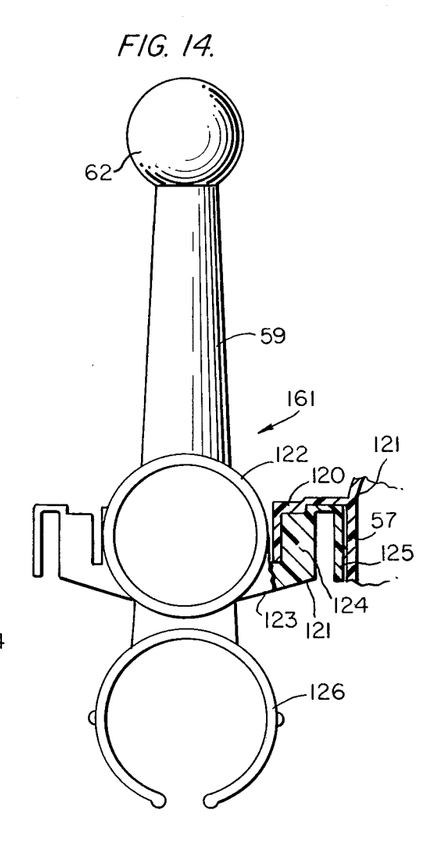
FIG. 14 is a view of the hanger fixture.
Figure 15:
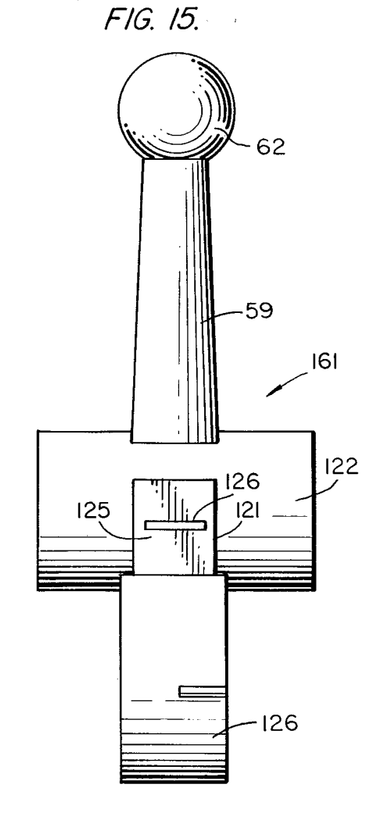
FIG. 15 is a 90° different view of the hanger fixture shown in FIG. 14.

Leg 57 of manifold tee piece 60 is also supplied with a U-shaped means 120 for achieving attachment to a mating means 121 positioned on each side of the tubular portion 122 of the connector hanger 61 as can be readily seen from FIGS. 14 and 15.

The portion in cross-section of FIG. 14 is designed to provide good details with regard to the snap fit accomplished between the U-shaped means 120 on the mainfold tee piece and the mating mean 121 on the connector hanger 61. The mating means includes an extension 123 extending from the hanger 61. The extension terminates in a vertical block like means 124, which is spaced from the connector and is adapted and constructed to accept the base portion of the U-shaped means 120. The legs of the U-shaped member embrace the side portions of the said vertical block like means 124. The block like means 124 has an L-shaped downwardly facing extension 125 which also extends radially from said connector 61. The longer leg of the L-shaped extension 125 has its outer surface in abutment with a wall portion of leg 57. The L-shaped extension is spring like so that it, together with the block means 124 through mating means 121, holds the leg 57 and thereby the manifold tee piece to the connector 61. A horizontally disposed short projection 126 assists in achieving a good friction fit.

The connector hanger 61 is also provided with an arcuate spring clamping means 126 for clamping about a tubular mean, (not shown).

Attention is now directed to exhaust valve body 63. The exhaust valve body 63 can be seen in particularity in a number of the figures; namely, FIGS. 2, 5, 8, and 9. The device consists of a cylindrical housing 56 having an egress port tube 64 of fairly large dimension and being adapted and constructed to having a flexible conduit attached thereto. Egress port tube 64 emanates from the cylindrical wall of the cylindrical housing 56. Furthermore it possesses the same dimensions as the legs 69 of the manifold tee piece 60 and has similar detents 79.

The upper end of the exhaust valve body has an upstanding relatively large diameter ingress port tube 65. Concentrically outwardly spaced therefrom is an extension 66 of the cylindrical wall of the cylindrical housing 56. There is thereby an annular space 67 defined externally between the ingress port tube 65 and internally with the concentric extension 66 into which the downwardly depending leg means 57 of the second tee is fitted and held by a bead 68 internally of the extension 66 in like manner as the complementary mating appendages between the leg of the manifold tee piece 60 and the nebulizer 11.

The exhaust valve body 63 has an annular roof portion 70 from which the underside thereof depends an elongated cylindrical wall 71 terminating in an open portion and a downwardly depending edge which acts as a valve seat 72 against which a disc diaphragm valve 73 is seated. The peripheral annular wedge shaped edge 34 of the diaphragm valve is sandwiched between a closure 74 for the valve means and the downwardly facing edge 75 of the cylindrical housing 56 which has a complementary wedge accepting annular recess 75a. The closure 74 has upwardly extending skirt 76 that embraces externally a lower portion of the cylindrical housing 56, and is supplied with a detent 77 retaining means.

For a better understanding of the valve arrangement and the fact that the diaphragm valve of the present invention has an unusual configuration, attention is directed to FIG. 8. This figure shows the diaphram valve 73 in greater detail. First of all it will be noted that the valve seat has its edges 72a and 72b bevelled on both sides to form an angle of 150°. The diaphragm has a centrally located disc portion. The V-section 73b has sloping walls 73c and 73d of thickened portions terminating at the open 73e with a less thickened portion, all complementary to the valve seat edges. The sloping walls 73c and 73d are essentially parallel to the mentioned bevelled edges 72a and 72b of the valve seat. Outwardly beyond the said V-section 73b is a downwardly extending annular loop portion 73f designed to provide flexibility. Outwardly beyond the said loop is the annular wedge shaped edge 34.

The closure 74 is supplied with a conduit means 78 to communicate with the space defined by the underside of the diaphragm valve 73 and the internally facing side of the closure 74. The diaphragm is maintained in a seated position by controlling the gas pressure in said space through a supply of gas through conduit 78. When the pressure in the tees and the exhaust valve body exceeds the pressure supplied into said space the diaphragm is upset to dump gases annularly of cylindrical wall 71 and internally of cylindrical housing 56 in a direction for exhaustion through egress port 64.

In the system shown in FIGS. 1 and 2, gas may be supplied through the open ends of the tees in either direction. Suitable flexible conduits may be attached, e.g. one from a source of gas and one directed to a patient through suitable conventional distribution means. In such a format, the nebulizer is designed to entrain in the main through stream supply of gas, a quantity of gas which has an increased water content.

In the embodiment of FIG. 5, the second tee has been replaced with an elbow so that the gas emanating through the nebulizer becomes the main source of breathing gas as the other side of the said first tee is adapted to be connected to a tubular conduit leading to a patient.

An optional valuable feature for the nebulizer is to supply it either with an extension of the cylindrical body 12 to a distance so that it extends beyond the conduit 18 extending from the bottom. Better yet, is the positioning of three equispaced legs 52 as shown in FIG. 2.

The system contemplated where the nebulizer of the present invention may be employed is an IPPB, i.e. intermittent positive pressure breathing apparatus. The nebulizer may be in one line segment to the patient while the pressure relief valve may be remote therefrom in another segment. It will be appreciated that the tees of the present invention, the elbow configuration, the exhaust valve means and, of course, most importantly, the nebulizer may be combined into various configurations and assemblies all designed to deliver to the patient a liquid with or without additional medicament as an aerosol. More about will be elucidated below.

Attention is now directed to FIGS. 6 and 19 for another embodiment of the nebulizer 80 of the present invention. This nebulizer comprises three basic components, namely a bottom cup shaped housing 81, a top cover housing 82 and secured there between a funnel-like arrangement 83.

The bottom cup shape housing 81 is open at the top, has a downwardly sloping bottom 84, terminating in a concentrically downwardly externally extending tubular stub 85 to which a pressurized gas carrying flexible conduit (not shown) is attached when said device is in its operational mode. Said bottom 84 has three equidistantly spaced downwardly depending legs 86 which extend beyond the end of the tubular stub 85.

The upper outwardly facing cylindrical wall 87 of the bottom cup shaped housing 81 has a screw lug 88 adapted and constructed to engage with the inwardly facing opening 90 of the lower portion of cylindrical wall 91 of the top cover housing 82.

The top cover housing is supplied internally with a shoulder 92 which is adapted and constructed be in confrontation with upwardly extending edge 93 of the bottom cup shaped housing 81.

A radially extending annular flange 94 of the funnel like arrangement 83 is sandwiched inbetween the shoulder 92 and upwardly extending edge 93 when said top cover housing 82 is screwed onto the bottom cup shaped housing 81.

The radially extending annular flange 94 has adjacent thereto a concentric longitudinally extending flange 95 which lies against the inner side of walls 87 and 91 to accomplish a leak tight fit. The funnel-like arrangement 83 has a downwardly inwardly sloping wall 96, terminating in an axially extending tubular element 97 which projects below the sloping wall 96 to a short distance above the bottom 84 and extends above said sloping wall 96 to a point above a nozzle 98 which projects axially inwardly from said bottom 84 and is essentially a continuation of tubular stub 85.

The tubular element 97 has dimensions whereby it is spatially displaced about said nozzle and is maintained therein by a plurality of tabs 97*a* internally of the tubular element 97. The tubular element 97 has an opening 100 in axial alignment with the opening 101 of the nozzle in a similar manner as in the first embodiment.

Centrally of the inside underside 102 of the top cover housing 82 is a baffle arrangement and projection similar to the one in the aforementioned embodiment. Additionally the nozzle and the tubular element about the nozzle are given a similar construction as in the first embodiment.

Similarly, the top cover housing 82 has an upwardly extending egress tubular stub 104 of relatively large diameter.

As an example of the various configurations of utilization of the various components, attention is directed to FIG. 2, for instance. In the noted assembly it will be seen that breathing gas is transmitted through a conventional corrugated flexible conduit 110 which is attached to one end of a tee conduit 60. The leg of the tee conduit 60 is secured to a nebulizer of the present invention as illustrated in FIG. 2. The other end of the tee 60 is frictionally engaged to a connector 61. An end of a second tee 60 is attached in the same manner to the other side of the connector. The leg of the second tee 60 is attached to an exhaust valve means 63, described in the above and further exemplified in FIG. 2.

A relatively small tee piece 111 is attached to tubular stub 18 to which a flexible conduit 112 is attached at one leg which carries the pressurized gas usually oxygen to be entrained with water by the nebulizer. Conduit 112 is attached to corrugated flexible conduit 110 for convenience to a supply of gas. Another flexible conduit 113 communicates the pressurized gas between the small tee piece 111 and the conduit means 78 the conduit 113 has a constriction 113a therein. The pressurized gas distributed to the underside of diaphragm valve 73 retains that valve in a closed position unless the pressure in the system exceeds the pressure of the pressurized gas.

The other end of the second tee has a conduit attached thereto for distribution to a patient.

When the pressure in the assembly is greater than the pressurized gas the valve 73 will be unseated and the gases will be dumped from egress port tube 64.

Figure 16:
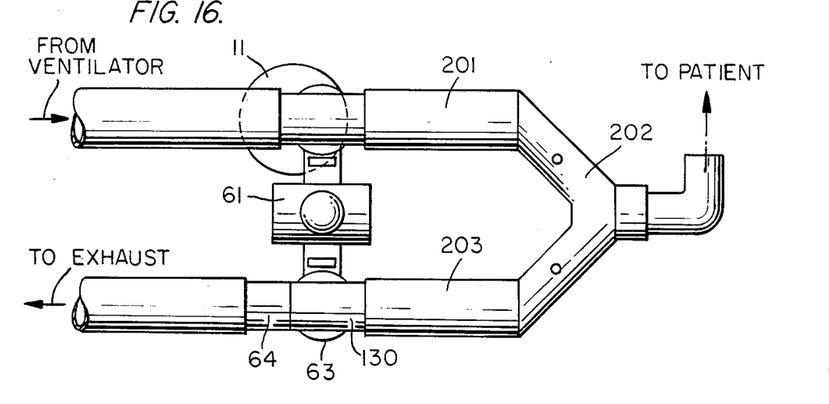
FIG. 16 is a top plan diagrammatical view of some of the various components when used in conjunction with a volume ventilator.
Figure 17:
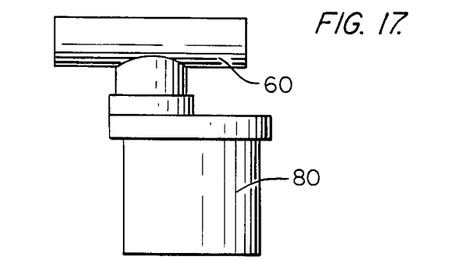
FIG. 17 is a side diagrammatical view of some of the various components when used in conjunction with a hand held nebulizer.
Figure 18:
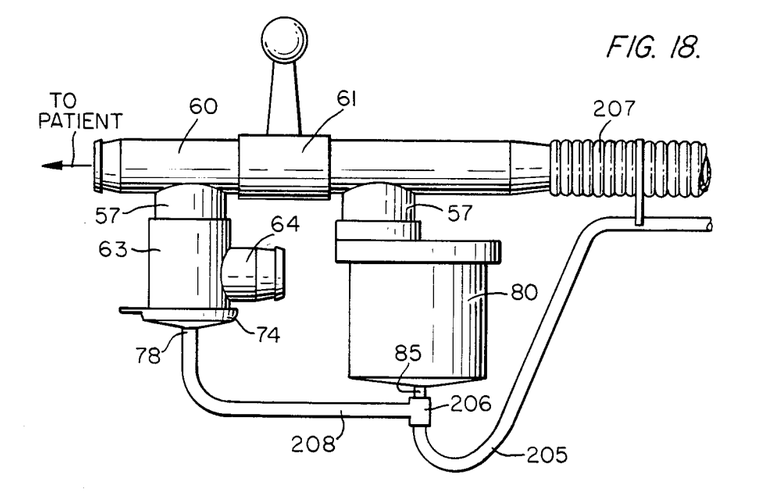
FIG. 18 is a side diagrammatical view of some of the various components when used in conjunction with an intermittent positive pressure breathing device.
Figure 19:
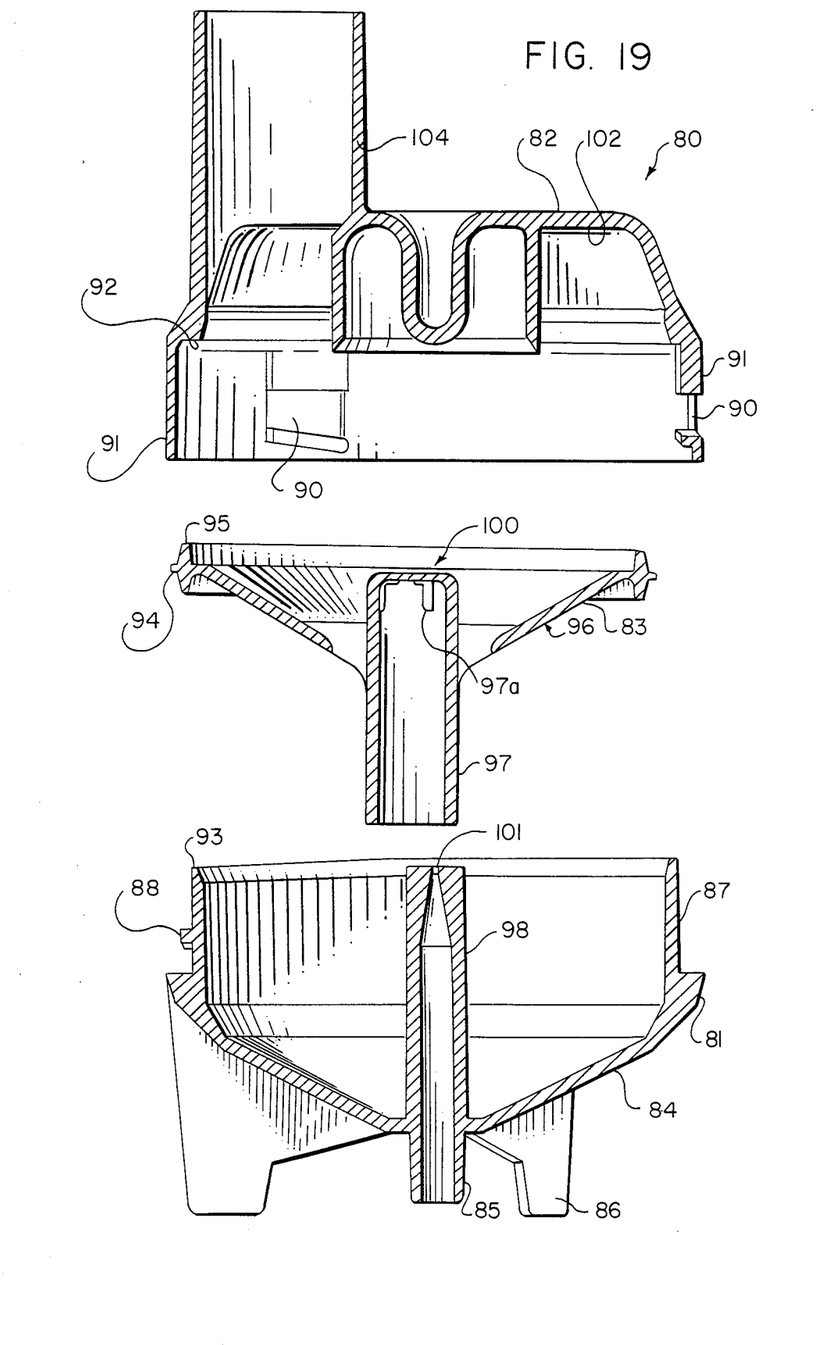
FIG. 19 is an exploded cross sectional view of the second embodiment as shown in FIG. 6.

To demonstrate how the nebulizer and the exhaust valve body may be employed in various configuration attention is now directed to FIGS. 16, 17 and 18.

FIG. 16 depicts a top plan view, somewhat diagrammatically, of a volume ventilator system. A conventional breathable gas carrying conduit 200 is connected to one side of the manifold tee piece of the present invention. The depending leg thereof is operatively connected to one of the nebulizer embodiments of the present invention 11 or 80. The other side of the manifold tee piece is operatively connected to one end of another tubular conduit 201; the other end of which is connected to a "Y" connector 202. One leg of this connector is suitably connected to a conventional terminal for presentment of the gases to a patient such as a face mark (not shown). The third leg of the "Y" connector is attached at one end to yet another tubular conduit 203. The other end is operatively connected to elbow connector 130. The double walled portion is connected to the exhaust valve body 63 as hereinbefore explained. A final tubular conduit 204 has one end connected to the egress port tube 64 of the exhaust valve body 63 and terminates at a suitable exhaust position.

For convenience, the manifold tee piece 60 is secured to one side of connector hanger 61 while elbow connector 130 is secured to the other side through the means discussed in the above.

The system shown in FIG. 17 is relatively simple. Depicted thereby is the use of a nebulizer 11 or 80 of the type disclosed herein. The egress port 44 is secured to the leg 57 of a manifold tee piece 60. One of the ends of the manifold tee piece is conventionally and operationally secured to a suitable face mask.

The set-up shown in FIG. 18 is somewhat more complex in that an intermittent positive pressure breathing system is presented. To both sides of a hanger connector 61, first and second manifold tee piece are operatively connected thereby providing a straight through passageway from the right to the left as shown by the FIG. 18. At the far right of the first manifold tee piece 60, one end of a conventional corrugated tube 207 is attached carrying gases for patient inhalation. The downwardly depending leg 57 of the first manifold tee piece has secured to it one or the other of the nebulizer 11 or 80 of the present invention. The downwardly depending leg 57 of the second manifold tee piece is operatively attached to an exhaust valve body 63. The other end of the second manifold tee piece not attached to either the connector hanger nor the exhaust valve body is attached to tubular means directed to the patient.

A supply line tube 205 of smaller diameter carries oxygen or air under pressure to one leg of a tee fitting 206. The second leg of the tee fitting is operatively secured to conduit 85 in the bottom 81 of the nebulizer 80. The third leg is secured to a conduit 208 which in turn is connected to conduit 78 in the cap 74 of the exhaust valve body to pressure into a closed position the diaphragm valve. The gas flowing thereinto is designed to drive the nebulizer.

If back pressure builds up in the conduits to the patient greater than that in the supply line 205 the exhaust valve body is designed to dump the excess. The pressures are adjusted whereby the gases delivered to the patient is intermittent, that is between expiration.

It will be appreciated that the components of the present invention may be usefully employed to achieve a number of systems so that a hospital may carry a minimum of inventory. The parts are fabricated of relatively inexpensive plastic materials, therefore, they may be disposed after a single use. Other uses for the component parts will come to mind, therefore the suggested uses are not to be considered limiting but merely suggestive.

What is claimed is:

1. A nebulizer for converting liquid into aerosol, comprising:
a housing having an open top end, said housing having a bottom, an elongated nozzle extending into said housing through said bottom said nozzle adapted and constructed to distribute gas under pressure into said housing, said housing being closed at said open top end with a fluid directing component having a funnel configuration extending downwardly forming an apex into said housing, said housing, said bottom and said fluid directing component adapted and constructed to define a liquid reservoir, said fluid directing component also having downwardly depending therefrom an open ended conduit adapted and constructed to encompass said nozzle in spaced relationship from the nozzle, said conduit means being adapted and constructed to communicate with the space between said conduit and said nozzle and said housing at the bottom portion thereof, said conduit extending upwardly above the apex of the funnel means and terminating in an end having a wall which has an opening therethrough in axial alignment with said nozzle, said funnel means being closed across substantially its widest opening with a cap, said cap having an egress port, the underside of said cap having a protrusion extending downwardly and terminating with a rounded end and in axial spaced relationship with said end of said conduit extending upwardly above the apex of the funnel means, whereby entrained liquid in said gas is distributed against said rounded end, the underside of said cap having a downwardly depending baffle surrounding said protrusion in spaced relationship therewith.

2. The nebulizer of claim 1 wherein the baffle has a downwardly facing edge which is bevelled radially outwardly and downwardly.

3. The nebulizer of claim 2 wherein the baffle and protrusion are connected by an arcuate portion.

4. The nebulizer of claim 3 wherein the portion around the apex of the funnel means is supplied with at least one opening whereby liquid may pass downwardly therethrough.

5. The nebulizer of claim 4 wherein the bottom of the housing comprises a series of downwardly stepped portions.

6. The nebulizer of claim 5 wherein the nozzle terminates below said housing and said housing has feet means whereby the nebulizer may be supported on a flat surface.

7. The nebulizer of claim 6 wherein the housing is cylindrical and the nozzle, the said conduit and said housing are concentric with one another.

8. The nebulizer of claim 7 wherein the said portion around the apex is in a flat annular plane.

9. The nebulizer of claim 1 wherein the nozzle has an upwardly facing opening of a smaller diameter than the opening of the upwardly facing conduit.

10. The nebulizer of claim 9 wherein the widest portion of the funnel means has an annular flange which is sandwiched between the cylindrical housing and the cap.

11. The nebulizer of claim 10 wherein means is provided internally of said conduit to retain said nozzle and said conduit of said funnel means in spaced relationship.

12. A patient gas-moisture delivery system comprising a tubular means being connected at one end to a supply of gas, a nebulizer mounted in operative communication with said tubular means, said nebulizer having a housing, said housing having an open top end, said housing having a bottom, an elongated nozzle extending into said said housing through said bottom, said nozzle adapted and constructed to distribute gas under pressure into said housing, said housing being closed at said open top end with a fluid directing component having a funnel configuration extending downwardly forming an apex into said housing, said housing, said bottom and said fluid directing component adapted and constructed to define a liquid reservoir, said fluid directing component also having downwardly depending therefrom an open ended conduit adapted and constructed to encompass said nozzle in spaced relationship from the nozzle, said conduit means being adapted and constructed to communicate with the space between said conduit and said nozzle and said housing at the bottom portion thereof, said conduit extending upwardly above the apex of the funnel means and terminating in an end having a wall which and an opening therethrough in axial alignment with said nozzle, said funnel means being closed across substantially its widest opening with a cap, said cap having and egress port, the underside of said cap having a protrusion extending downwardly and terminating with a rounded end and in axial spaced relationship with said end of said conduit extending upwardly above the apex of the funnel means, whereby entrained liquid in said gas is distributed against said rounded end, the underside of said cap having a downwardly depending baffle surrounding said protrusion in spaced relationship therewith; an exhaust valve body also being mounted in operative communication with said tubular means, said exhaust valve body comprising a tubular housing, said tubular housing having a top and an inner concentrically disposed tube, said tube having a portion extending upwardly above said top and said portion adapted and constructed to be in communication with a tubular conduit, said tubular housing and said tube terminating at the bottom in essentially the same plane, a flexible diaphragm positioned across said bottom of said tube and in fixed abutment against said bottom of said tubular housing, said diaphragm having a flange portion, a cap having an upwardly extending skirt, said flange portion of said diaphragm being sandwiched between said skirt and the bottom of said tubular housing, said cap and said diaphragm defining a space, said cap having a port means, said tubular housing having a port means, said bottom of said tube adapted and constructed to be a valve seat for said diaphragm; primary gas carrying conduit means operatively attached to said nozzle of said nebulizer for introduction of gas under pressure into said nebulizer and a secondary gas carrying conduit means connected at one end in operative association to said primary gas carrying conduit means and another end to said port means of said cap.

13. The system of claim 12 wherein said tubular means having said nebulizer and said exhaust valve body is supported by a hanger means, said hanger means comprising a cylindrical tube member extending radially from said tube, attachment means secured to said cylindrical member adapted and constructed to retain said tubular means, said attachment means including a radially extending portion attached to said cylindrical tube, said radially extending portion being spaced from said cylindrical tube by a slot facing in one direction, said radially extending portion having a slot facing in an opposite direction.

* * * * *